United States Patent
Oleynikov et al.

(10) Patent No.: US 7,339,341 B2
(45) Date of Patent: Mar. 4, 2008

(54) SURGICAL CAMERA ROBOT

(75) Inventors: Dmitry Oleynikov, Omaha, NE (US);
Shane M. Farritor, Lincoln, NE (US);
Mark E. Rentschler, Omaha, NE (US);
Stephen R. Platt, Garland, NE (US);
Jason Dumpert, Omaha, NE (US)

(73) Assignee: Board of Regents of the University of Nebraska, Lincoln, NE (US)

( * ) Notice: Subject to any disclaimer, the term of this patent is extended or adjusted under 35 U.S.C. 154(b) by 0 days.

(21) Appl. No.: 11/403,756

(22) Filed: Apr. 13, 2006

(65) Prior Publication Data

US 2006/0198619 A1 Sep. 7, 2006

Related U.S. Application Data

(63) Continuation-in-part of application No. 10/616,096, filed on Jul. 8, 2003, now Pat. No. 7,042,184.

(51) Int. Cl.
*B25J 5/00* (2006.01)
*G03B 4/00* (2006.01)

(52) U.S. Cl. .................. 318/568.12; 318/568.11; 128/899; 398/14

(58) Field of Classification Search ........ 318/567–590; 606/1, 205, 300, 428, 407; 700/258, 251
See application file for complete search history.

(56) References Cited

U.S. PATENT DOCUMENTS 3,870,264 A 3/1975 Robinson (Continued)

FOREIGN PATENT DOCUMENTS

JP 07306155 11/1995

(Continued)

OTHER PUBLICATIONS

Fireman, Z. et al. "Diagnosing small bowel Crohn's disease with wireless capsule endoscopy." *Gut Online*. 2003, 52: 390-392. BMJ Publishing Group Ltd.

(Continued)

*Primary Examiner*—Paul Ip
(74) *Attorney, Agent, or Firm*—Paegre & Benson LLP

(57) ABSTRACT

The present invention is a miniature camera robot which can be placed entirely within an open space such as an abdominal cavity. The instant camera robot has pan and tilt capabilities, an adjustable focus camera, and a support component for supporting the robot body. In particular embodiments, the camera robot further contains a light source for illumination and a handle to position the camera robot. A system and method for using the instant camera robot are also provided.

20 Claims, 2 Drawing Sheets

U.S. PATENT DOCUMENTS

| | | | |
|---|---|---|---|
| 4,568,311 A | 2/1986 | Miyake | 464/109 |
| 4,852,391 A | 8/1989 | Ruch et al. | 73/40.5 R |
| 5,172,639 A | 12/1992 | Wiesman et al. | 104/138.2 |
| 5,201,325 A * | 4/1993 | McEwen et al. | 600/587 |
| 5,271,384 A * | 12/1993 | McEwen et al. | 600/201 |
| 5,284,096 A | 2/1994 | Pelrine et al. | 104/138.2 |
| 5,304,899 A | 4/1994 | Sasaki et al. | 318/16 |
| 5,307,447 A * | 4/1994 | Asano et al. | 700/255 |
| 5,363,935 A | 11/1994 | Schempf et al. | |
| 5,382,885 A | 1/1995 | Salcudean | |
| 5,388,528 A | 2/1995 | Pelrine | 105/78 |
| 5,436,542 A * | 7/1995 | Petelin et al. | 318/567 |
| 5,674,030 A * | 10/1997 | Sigel | 405/184.2 |
| 5,736,821 A * | 4/1998 | Suyama | 318/16 |
| 5,845,646 A | 12/1998 | Lemelson | 128/899 |
| 5,878,783 A | 3/1999 | Smart | 138/93 |
| 6,031,371 A | 2/2000 | Smart | |
| 6,058,323 A | 5/2000 | Lemelson | 600/408 |
| 6,107,795 A | 8/2000 | Smart | 324/220 |
| 6,132,368 A * | 10/2000 | Cooper | 600/102 |
| 6,159,146 A | 12/2000 | El Gazayerli | 600/106 |
| 6,162,171 A | 12/2000 | Ng et al. | 600/141 |
| 6,286,514 B1 | 9/2001 | Lemelson | 128/899 |
| 6,293,282 B1 | 9/2001 | Lemelson | 128/899 |
| 6,309,403 B1 | 10/2001 | Minor et al. | 606/205 |
| 6,321,106 B1 | 11/2001 | Lemelson | 600/407 |
| 6,327,492 B1 | 12/2001 | Lemelson | 600/434 |
| 6,394,998 B1 * | 5/2002 | Wallace et al. | 606/1 |
| 6,400,980 B1 | 6/2002 | Lemelson | 600/478 |
| 6,450,104 B1 | 9/2002 | Grant et al. | 104/138.2 |
| 6,468,203 B2 | 10/2002 | Belson | 600/146 |
| 6,508,413 B2 | 1/2003 | Bauer et al. | |
| 6,512,345 B2 | 1/2003 | Borenstein et al. | 318/568.12 |
| 6,548,982 B1 | 4/2003 | Papanikolopoulos et al. | |
| 6,610,007 B2 | 8/2003 | Belson et al. | 600/146 |
| 6,648,814 B2 | 11/2003 | Kim et al. | 600/114 |
| 6,661,571 B1 * | 12/2003 | Shioda et al. | 359/372 |
| 6,687,571 B1 | 2/2004 | Byrne et al. | 700/245 |
| 6,692,485 B1 * | 2/2004 | Brock et al. | 606/1 |
| 6,702,734 B2 | 3/2004 | Kim et al. | |
| 6,714,841 B1 * | 3/2004 | Wright et al. | 700/259 |
| 6,719,684 B2 | 4/2004 | Kim et al. | 600/101 |
| 6,728,599 B2 * | 4/2004 | Wang et al. | 700/258 |
| 6,774,597 B1 | 8/2004 | Borenstein | |
| 6,783,524 B2 * | 8/2004 | Anderson et al. | 606/28 |
| 6,785,593 B2 * | 8/2004 | Wang et al. | 700/258 |
| 6,799,065 B1 * | 9/2004 | Niemeyer | 600/407 |
| 6,804,581 B2 * | 10/2004 | Wang et al. | 700/251 |
| 6,820,653 B1 | 11/2004 | Schempft et al. | |
| 6,824,508 B2 | 11/2004 | Kim et al. | |
| 6,824,510 B2 | 11/2004 | Kim et al. | |
| 6,832,988 B2 | 12/2004 | Sproul | |
| 6,860,346 B2 | 3/2005 | Burt et al. | |
| 6,870,343 B2 | 3/2005 | Borenstein et al. | |
| 6,917,176 B2 | 7/2005 | Schempf et al. | |
| 6,991,627 B2 * | 1/2006 | Madhani et al. | 606/1 |
| 7,042,184 B2 | 5/2006 | Oleynikov et al. | |
| 7,066,879 B2 | 6/2006 | Fowler et al. | |
| 7,126,303 B2 | 10/2006 | Farritor et al. | |
| 2001/0018591 A1 | 8/2001 | Brock et al. | 606/130 |
| 2002/0003173 A1 * | 1/2002 | Bauer et al. | 239/227 |
| 2002/0091374 A1 * | 7/2002 | Cooper | 606/1 |
| 2002/0103417 A1 | 8/2002 | Gazdzinski | |
| 2002/0111535 A1 | 8/2002 | Kim et al. | |
| 2002/0120254 A1 | 8/2002 | Julian et al. | |
| 2002/0140392 A1 | 10/2002 | Borenstein et al. | |
| 2002/0156347 A1 | 10/2002 | Kim et al. | 600/160 |
| 2002/0171385 A1 | 11/2002 | Kim et al. | |
| 2002/0173700 A1 | 11/2002 | Kim et al. | |
| 2002/0190682 A1 | 12/2002 | Schempf et al. | 318/568.11 |
| 2003/0045888 A1 | 3/2003 | Brock et al. | 606/130 |
| 2003/0089267 A1 | 5/2003 | Ghorbel et al. | 104/138.1 |
| 2003/0092964 A1 | 5/2003 | Kim et al. | |
| 2003/0167000 A1 | 9/2003 | Mullick et al. | |
| 2003/0172871 A1 | 9/2003 | Scherer | |
| 2003/0179308 A1 * | 9/2003 | Zamorano et al. | 348/333.12 |
| 2003/0230372 A1 | 12/2003 | Schmidt | 156/64 |
| 2004/0024311 A1 * | 2/2004 | Quaid, III | 600/428 |
| 2004/0034282 A1 * | 2/2004 | Quaid, III | 600/300 |
| 2004/0034283 A1 * | 2/2004 | Quaid, III | 600/300 |
| 2004/0034302 A1 * | 2/2004 | Abovitz et al. | 600/428 |
| 2004/0070822 A1 * | 4/2004 | Shioda et al. | 359/372 |
| 2004/0099175 A1 | 5/2004 | Perrot et al. | |
| 2004/0106916 A1 * | 6/2004 | Quaid et al. | 606/1 |
| 2004/0111113 A1 * | 6/2004 | Nakamura et al. | 606/205 |
| 2004/0140786 A1 | 7/2004 | Borenstein | 318/568.12 |
| 2004/0173116 A1 | 9/2004 | Ghorbel et al. | 104/138.2 |
| 2004/0254680 A1 | 12/2004 | Sunaoshi | 700/253 |
| 2005/0029978 A1 | 2/2005 | Oleynikov et al. | |
| 2006/0119304 A1 | 6/2006 | Farritor et al. | |
| 2006/0149135 A1 | 7/2006 | Paz | |
| 2006/0152591 A1 | 7/2006 | Ling | |
| 2006/0196301 A1 | 9/2006 | Oleynikov et al. | |

FOREIGN PATENT DOCUMENTS

| | | |
|---|---|---|
| WO | WO 02/082979 | 10/2002 |

OTHER PUBLICATIONS

Abbou, Clement-Claude et al. "Laparoscopic Radical Prostatectomy with a Remote Controlled Robot." *The Journal of Urology*. Jun. 2001, 165: 1964-1966.

Fraulob, S. et al. "Miniature assistance module for robot-assisted heart surgery." *Biomed. Tech.* 2002, 47 Suppl. 1, Pt. 1: 12-5.

Buber, A. E. et al. "Miniaturized Instrument Systems for Minimally Invasive Diagnosis and Therapy." *Biomedizinische Technik*. 2002, Band 47, Erganzungsband 1: 198-201.

Thomann, G. et al. "The Design of a new type of Micro Robot for the Intestinal Inspection." *Proceedings of the 2002 IEEE/RSJ Intl. Conference on Intelligent Robots and Systems EPFL*. Oct. 2002: 1385-1390.

Guo, Shuxiang et al. "Fish-like Underwater Microrobot with 3 DOF." *Proceedings of the 2002 IEEE International Conference on Robotics & Automation*. May 2002: 738-743.

Fukuda, Toshio et al. " Mechanism and Swimming Experiment of Micro Mobile Robot in Water." *Proceedings of the 1994 IEEE International Conference on Robotics and Automation*. 1994: 814-819.

Guo, Shuxiang et al, "Micro Active Guide Wire Catheter System-Characteristic Evaluation, Electrical Model and Operability Evaluation of Micro Active Catheter." *Proceedings of the 1996 IEEE International Conference on Robotics and Automation*. Apr. 1996: 2226-2231.

Yu, Sun et al. "Microrobotic Cell Injection." *Proceedings of the 2001 IEEE International Conference on Robotics & Automation*. May 2001: 620-625.

Ruurda, JP et al. "Robot-assisted surgical systems: a new era in laparoscopic surgery." *Ann. R. Coll. Surg. Engl.* 2002, 84: 223-226.

Menciassi, A. et al. "Robotic Solutions and Mechanisms for a Semi-Autonomous Endoscope." *Proceedings of the 2002 IEEE/RSJ Intl. Conference on Intelligent Robots and Systems EPFL*. Oct. 2002: 1379-1384.

Ishiyama, K. et al. "Spiral-type Micro-machine for Medical Applications." *2000 International Symposium on Micromechatronics and Human Science*. 2000: 65-69.

Fearing, R. S. et al. "Wing Transmission for a Micromechanical Flying Insect." *Proceedings of the 2000 IEEE International Conference on Robotics & Automation*. Apr. 2000: 1509-1516.

Mei, Tao et al. "Wireless Drive and Control of a Swimming Microrobot." *Proceedings of the 2002 IEEE International Conference on Robotics & Automation*. May 2002: 1131-1136.

Fireman, Z. et al. "Diagnosing small bowel Crohn's disease with wireless capsule endoscopy," *Gut Online*. 2003, 52: 390-392. BMJ Publishing Group Ltd.

Abbou, Clement-Claude et al. "Laparoscopic Radical Prostatectomy with a Remote Controlled Robot." *The Journal of Urology*. Jun. 2001, 165: 1964-1966.

Fraulob, S. et al. "Miniature assistance module for robot-assisted heart surgery." *Biomed. Tech.* 2002, 47 Suppl. 1, Pt. 1: 12-5.

Gurber, A. E. et al. "Miniaturized Instrument Systems for Minimally Invasive Diagnosis and Therapy." *Biomedizinische Technik.* 2002, Band 47, Erganzungsband 1: 198-201.

Worn et al., "Espirit Project No. 33915:Miniaturised Robot for Micro Manipulation (MINIMAN)", Nov. 1998 http://wwwipr.ira.uka.de/-microbot/miniman/.

Meron, G., "The development of the swallowable video capsule (M2A)," Gastrointestinal Endoscopy 2000 52, 6:817-819.

Phee et al., "Development of Microrobotic Devices for Locomotion in the Human Gastrointestinal Tract", International Conference on Computational Intelligence.

Breda et al., "Future developments and perspectives in laparoscopy", Eur. Urology 2001 40, 1:84-91.

Strong, et al. "Efficacy of Novel Robotic Camera vs a Standard Laparoscopic Camera," Surgical Innovation vol. 12, No. 4, Dec. 2005, Westminster Publications, Inc., pp. 315-318.

Marcia Yu, BSN, RN, "M2ATM Capsule Endoscopy A Breakthrough Diagnostic Tool for Small Intestine Imaging," vol. 25, No. 1, Gastroenterology Nursing, pp. 24-27, no date.

Andrew Miller, Ph.D., et a., "In-Vivo Stereoscopic Imaging System with 5 Degrees-of-Freedom for Minimal Access Surgery," Dept. of Computer Science and Dept. of Surgery, Columbia University, New York, NY pp. 7, no date.

U.S. Appl. No. 60/180,960, filed Feb. 2000.

Park et al., "Trocar-Less Instrumentation for Laproscopy-Magnetic positioning of Intra-abdominal Camera and Retractor," Annals of Surgery, vol. 25, No. 3, pp. 379-384, Mar. 2007.

Schwartz, "In the Lab: Robots That Slink and Squirm," The New York Times, 4 pp., Mar. 7, 2007.

\* cited by examiner

SURGICAL CAMERA ROBOT

INTRODUCTION

This application is a continuation-in-part of U.S. patent application Ser. No. 10/616,096 filed Jul. 8, 2003, now U.S. Pat. No. 7,042,184, issued May 9, 2006, the contents of which are incorporated herein by reference in its entirety.

BACKGROUND OF THE INVENTION

Surgical laparoscopic robots are currently used to maneuver instruments with high precision allowing micro-scale tasks otherwise not possible. Despite these successes, the benefits of laparoscopy are generally limited to less complex procedures because the surgeon loses the ability to manipulate tissue and visualize the surgical field from multiple angles.

From the point of view of a surgeon, minimally invasive surgery is minimal access surgery (Tendick, et al. (1998) *IEEE/ASME Trans. Mechatron.* 3(1):34-42). Reduced access reduces dexterity, limits perception, increases strain and the likelihood of error, and lengthens procedure times (Falcone & Goldberg (2003) *Clin. Obstet. Gynecol.* 46(1): 37-43; Li, et al. (2000) *Comp. Aid. Surg.* 5:326-332; Tendick, et al. (1998) *IEEE/ASME Trans. Mechatron.* 3(1):34-42). The operative field is visualized through an electronic interface, and tissue manipulation is performed with long instruments that impose severe ergonomic limitations (Li, et al. (2000) *Comp. Aid. Surg.* 5:326-332). The long, rigid instruments and cameras typically used in laparoscopic surgery are constrained to only four degrees of freedom (three rotations and in-out translation) through the entry incision. This prevents orienting the tool tips arbitrarily. Dexterity is significantly reduced because of the lost degrees of freedom and because of motion reversal due to the fulcrum effect at the entry point (Cavusoglu, et al. (2003) *Indust. Robot: Intl. J.* 30(1): 22-29).

Vision limitations are significant (Tendick, et al. (1996) In: Computer Integrated Surgery: Technology and Clinical Applications; Treat (1996) In: Computer Integrated Surgery: Technology and Clinical Applications) because the current field of view cannot encompass the frequent changes of instruments as they pass through the abdominal cavity. This has led to accidental injury to organs and vascular structures (Southern Surgeons Club (1991) *N. Engl. J. Med.* 324:1073-1078; Wolfe, et al (1991) *Arch. Surg.* 126:1192-1998). Additional viewpoints showing the entire body cavity have been suggested as being helpful (Schippers & Schumpelick (1996) In: Computer Integrated Surgery: Technology and Clinical Applications). Mobility limitations are significant and lead to patient complications because it is not possible for the surgeon to compensate for the lost degrees of freedom during complex tasks (e.g., suturing) (Tendick, et al. (1996) supra). These limitations have impeded the use of laparoscopy.

Dexterity constraints also prevent the optimal placement of the camera used to visualize the abdominal cavity while preparing for and performing surgery. Obstructed or incomplete visual feedback can contribute to a variety of complications. Common complications while inserting access ports and during the surgical procedure itself include aortic and vascular injury, pneumothorax, and bowel perforations (Kazemier, et al. (1998) *J. Am. Coll. Surg.* 186(5):604-5; Leggett, et al. (2002) *Surg. Endoscopy* 16(2):362; Munro (2002) *Curr. Opin. Obstet. Gynecol.* 14(4):365-74; Orlando, et al. (2003) *J. Laparoendo. Adv. Surg. Techn.* 13(3):181-184).

The challenges associated with performing laparoscopic procedures are graphically illustrated by the fact that under identical experimental conditions, suturing a square knot with laparoscopic tools takes almost twice as long as with hand tools in open surgery (Tendick, et al. (1993) *Presence* 2:66-81). Until visual feedback and dexterity improve, the enormous potential for minimally invasive surgery to replace many open conventional procedures will not be fully realized.

Surgical imaging devices exist, but do not provide the range of vision needed to provide adequate visual feedback to improve dexterity. A miniature disposable imaging capsule has been developed. See U.S. patent application Ser. No. 09/759,398. The capsule is swallowed by the patient and, with the natural movement of bowel, it passively moves through the gastrointestinal tract, and is passed naturally out of the body. The capsule transmits information (such as imaging information) to a receiver worn by the patient, which is later processed on a computer. The capsule consists of lens, illuminating LEDs, imager, battery, transmitter, and antenna. However, this device was designed for use in colonoscopy and would not function well in an open abdominal cavity during laparoscopic surgery.

U.S. patent application Ser. No. 10/672,274 teaches a device for imaging anatomical structures in a videoendoscopic surgery training system. The device comprises a digital video camera disposed within a practice volume; and a support structure comprising an elongate member having a proximal end disposed outside of the practice volume, and a distal end disposed inside the practice volume, the digital video camera being coupled with the distal end of the elongate member. The support structure comprises a bracket configured to enable the elongate member to pan and tilt. A light source is also disclosed to illuminate the anatomical structure.

Needed in the art is an imaging device for enhanced surgical field visualization from multiple angles within an open space such as the abdominal cavity. The present invention meets this need by providing a camera robot, the whole of which can be placed within the open abdominal cavity, to supply visual feedback to a surgeon during surgical procedures without the need for additional incisions to accommodate the imaging system.

SUMMARY OF THE INVENTION

The present invention is a camera robot for internal imaging. The camera robot is composed of a robot body with a camera disposed therein; an adjustable-focus camera component; a pan or tilt camera component; and a support component for supporting the robot body, wherein said camera robot is produced from a material capable of being sterilized. The instant camera robot is an improvement over existing imaging systems as the whole of the camera robot body is capable of being introduced into an open space to be imaged. In one embodiment, the camera robot has a handle. In another embodiment, the camera robot is used in combination with a laparoscopic surgical tool, wherein the camera robot is adapted to fit through a port of the laparoscopic surgical tool. In still other embodiments, the whole of the instant camera robot is introduced into an open space to obtain internal images.

DETAILED DESCRIPTION OF THE INVENTION

The increased use of laparoscopy has led to a dramatic shift in surgical methods and improvements in patient care. Laparoscopic surgery avoids the trauma traditionally inflicted in gaining access to the abdominal organs by using long, rigid instruments and cameras inserted into the body through small incisions. Maneuvering space for the tools used is created by insufflating $CO_2$ to lift the abdominal wall away from the organs. The reduced surgical invasiveness in laparoscopic surgery results in fewer complications and a more rapid recovery for the patient. The adoption of laparoscopic techniques has been driven by technological advances such as robots. Surgical laparoscopic robots currently are used to maneuver and position instruments with high precision and allow micro-scale tasks otherwise not possible. Despite these successes, however, laparoscopy remains constrained in application due to the loss of sensory feedback, limited imaging and the reduced mobility and dexterity associated with conventional approaches. Current laparoscopes use rigid, single view cameras inserted through a small incision. Such cameras have a limited field of view with highly constrained motion. To obtain a new perspective using such a camera often requires the removal and reinsertion of the camera through another incision thereby increasing patient risk.

Figure 1:
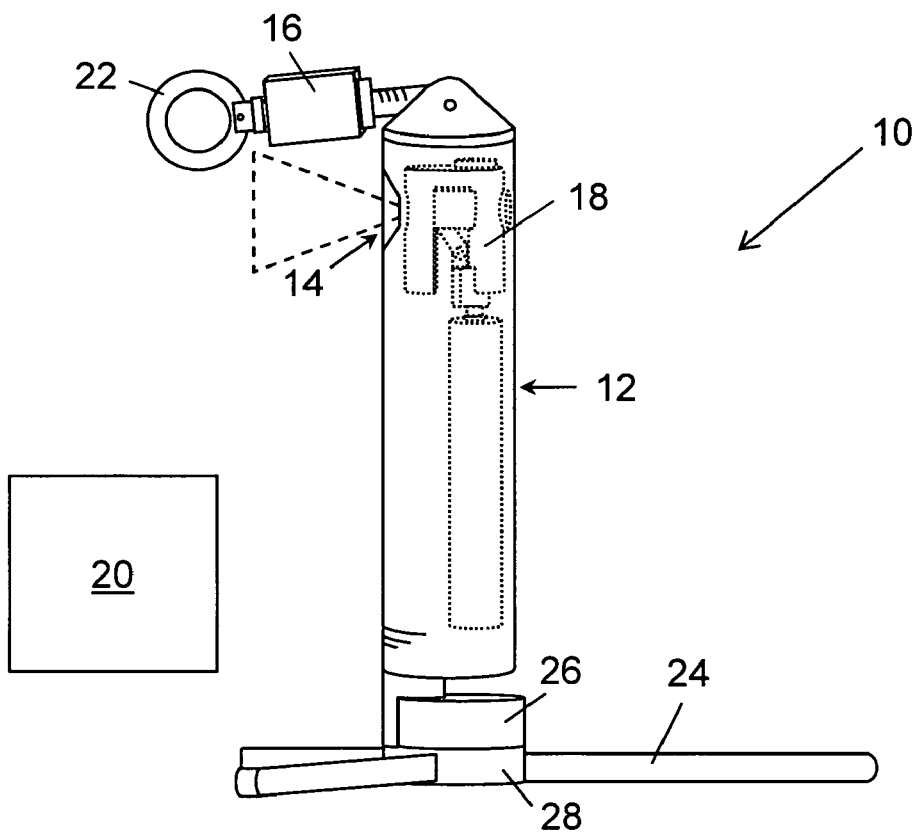
FIG. 1 depicts a side view of a robot camera 10 in the deployed in vivo configuration. Torsion springs allow the support component 24 to be abducted after abdominal entry. Light source 16 provides illumination to the viewing field. Retractable handle 22 is within the viewing field to facilitate placement of the robot camera and removal from inside an animal's body.

The present invention facilitates the application of laparoscopy and other minimally invasive surgical techniques by providing a remote-control camera robot, the whole of which can be placed in an open space, e.g., within the abdominal cavity, to provide visual feedback during surgical procedures. As such, incisions and patient risk are minimized. Referring to FIG. 1, the instant camera robot 10 is composed of a robot body 12 with a camera 14 disposed therein, an adjustable-focus camera component 18, and support component 24 for supporting robot body 12 inside an open space (e.g., a body cavity). In particular embodiments, the instant camera further contains a light source 16 for illumination, a handle 22, and a controller 20 for controlling pan, tilt and/or focusing of camera 14. Advantageously, the camera robot of the present invention is self-contained, produced from commercially available components, and remote-controlled. As used in the context of the present invention, the term "remote-control" refers to the control of at least one activity or process of the robot camera from a distance. As such, the whole of the instant camera robot can be placed inside an open space with pan, tilt and/or adjustable focus capabilities externally controlled. Further, it is contemplated that multiple camera robots can be used simultaneously to provide the operator with improved visual feedback from arbitrary and, potentially multiple, viewing angles. Likewise, the instant camera robot can be used in conjunction with one or more surgical robots.

Robot body 12 of the instant camera robot 10 can take on many different configurations, such as cylindrical or spherical shapes so as to be compatible with laparoscopic tools known currently in the art. However, as with the other components, the body configuration of the robot of the present invention is not limited to that exemplified herein. In general, the only constraints on the shape of the body of the camera robot in various embodiments are that the body be able to incorporate the components of the robot and not cause trauma or damage to internal area being viewed. An exemplary camera robot is depicted in the accompanying figures, wherein the robot's diameter and length are 15 mm and 75 mm, respectively, to allow for use with a standard laparoscopic port.

In certain embodiments, robot body 12 has pan and/or tilt capabilities, thereby providing rotation about two independent axes. This allows the surgeon more in-depth visualization of the abdominal cavity for surgical planning and procedures. A component for panning can be achieved using a ball bearing mechanism or any other suitable mechanism well-known to the skilled artisan. A component for tilting can be achieved using a pin or ratchet mechanism or any other suitable mechanism well-known to the skilled artisan. In particular embodiments, the instant camera robot has a panning component up to 360°. In other embodiments, the instant camera robot has a panning component from 180° to 360°. In still other embodiments, the instant camera robot has a tilting component for tilting ±45° from vertical, i.e., a range of 90°.

Panning and tilting can be achieved manually (e.g., by a surgeon) or using standard mechanical technology to actuate panning and tilting. For example, independent permanent magnet DC motors (e.g., commercially available from MicroMo™ Electronics, Inc., Clearwater, Fla.) can be employed in combination with standard rotary-to-translatory couplings such as lead screws, gears, or pulleys. Other suitable devices which would be useful in alternative embodiments of the present invention include shape memory alloys, piezoelectric-based actuators, pneumatic motors, or hydraulic motors, or the like. Pneumatic and hydraulic motors are efficient, but the pump generally must be external to the robot. Thus, such motors may be useful in a tethered or wired embodiment of the present invention, but not in the wireless embodiment of the present invention.

Figure 2:
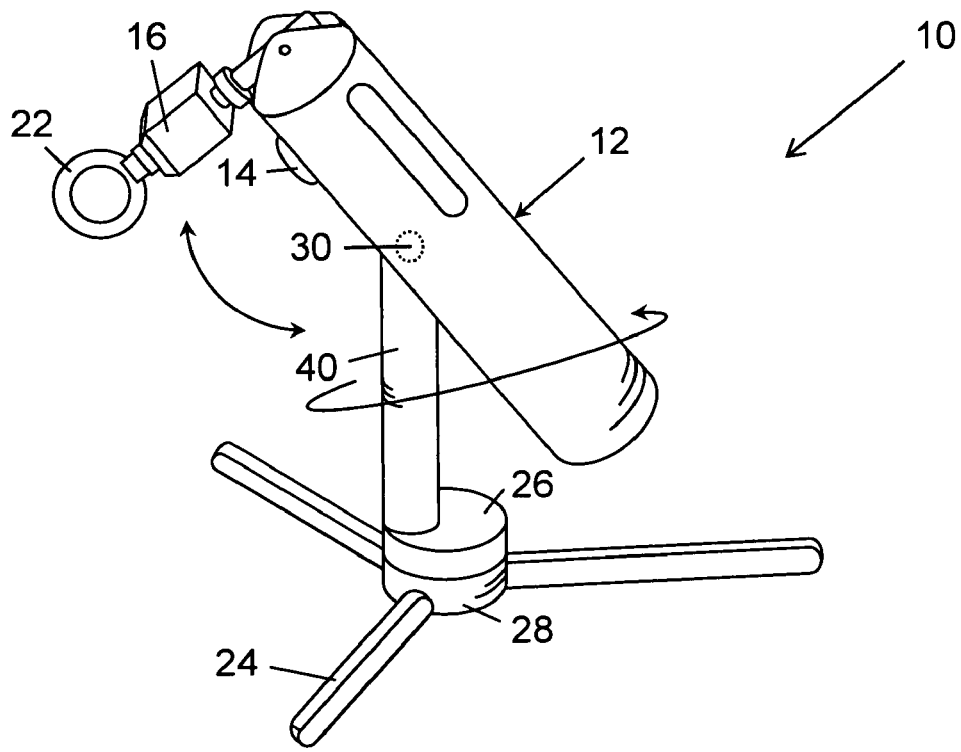
FIG. 2 depicts a side view of a robot camera 10 in the deployed in vivo configuration. Pan 360° and tilt ±45° of the robot body are shown with arrows.

As depicted in FIG. 2, the illustrate camera robot has a pan and tilt robot body 12 with a tilting component 30, and a panning component 26,28 which is composed of a small ball bearing structure 26 that is attached to a base 28 thereby allowing freedom of rotation. In accordance with the illustrative example, motors for actuating pan and tilt could be housed in robot body 12 and/or support 40.

In alternate embodiments, robot body 12 has a tilting component for tilting ±45° from vertical and camera 14, or components thereof (e.g., the imager or lens), has a panning component for panning up to 360° which is independent of robot body 12. Likewise, it is contemplated that robot body 12 has a panning component for panning up to 360° and the camera 14, or components thereof, has a tilting component for tilting ±45° from vertical which is independent of robot body 12. In still another embodiment, camera 14, or components thereof, has pan (e.g., up to 360°) and tilt (e.g., ±45° from vertical) component independent of robot body 12. Moreover, it is contemplated that the body or camera could be capable of a side-to-side motion (e.g., yaw).

Advantageously, the instant robot provides real-time video from a camera or imaging device during a minimally invasive surgical procedure. As used in the context of the present invention, the term "camera" or "imaging device" describes the imaging elements (e.g., lens and image sensor) and processing circuitry which is used to produce a video signal which can be accepted by a standard video device such as a television or video monitor accompanying a personal computer. The term "image sensor" as used herein describes the components of a solid state imaging device which captures images and stores them within the structure of each of the pixels in the array of pixels found in the imaging device. The timing and control circuits can be placed either on the same planar structure as the pixel array, in which case the image sensor can also be defined as an integrated circuit, or the timing and control circuitry can be placed remote from the pixel array. The terms "signal" or "image signal" as used herein, and unless otherwise more specifically defined, refer to an image which at some point during its processing by the imaging device, is found in the form of electrons which have been placed in a specific format or domain. The term "processing circuitry" as used herein refers to the electronic components within the imaging device which receive the image signal from the image sensor and ultimately place the image signal in a usable format. The terms "timing and control circuits" or "circuitry" as used herein refer to the electronic components which control the release of the image signal from the pixel array.

To show details important to the operator, the camera or imaging device of the instant invention has adequate resolution, field-of-view and lighting and alternatively, and depth of field and range of focus. Moreover, the instant camera can be a stereo camera to provide a three-dimensional image. Miniature cameras are commonly found in devices such as cellular phones and endoscopic tools. In this regard, the camera of the present invention can be any known in the art that is compatible with the various designs and configurations of the invention. For example, the camera of the instant robot can employ any common solid state image sensor including a charged coupled device (CCD), charge injection device (CID), photo diode array (PDA), or complementary metal oxide semiconductor (CMOS), which offers functionality with simplified system interfacing. For example, a particularly suitable CMOS imager including active pixel-type arrays is disclosed in U.S. Pat. No. 5,471,515. This CMOS imager can incorporate a number of other different electronic controls that are usually found on multiple circuit boards of much larger size. For example, timing circuits, and special functions such as zoom and anti-jitter controls can be placed on the same circuit board containing the CMOS pixel array without significantly increasing the overall size of the host circuit board. Furthermore, this particular CMOS imager requires 100 times less power than a CCD-type imager. The CMOS imager disclosed in U.S. Pat. No. 5,471,515 has enabled the development of a "camera on a chip." As such, many CMOS imagers can be manufactured at a fraction of the cost of other solid state imaging technologies. Suni Microsystems, Inc. (Mountain View, Calif.) has also developed a CCD/CMOS hybrid which combines the high quality image processing of CCDs with standard CMOS circuitry construction. In particular embodiments, the camera is a CMOS camera. In other embodiments, the camera has a variable focal length, which is manually or mechanically adjusted by an adjustable-focus camera component.

Figures 3, 4:
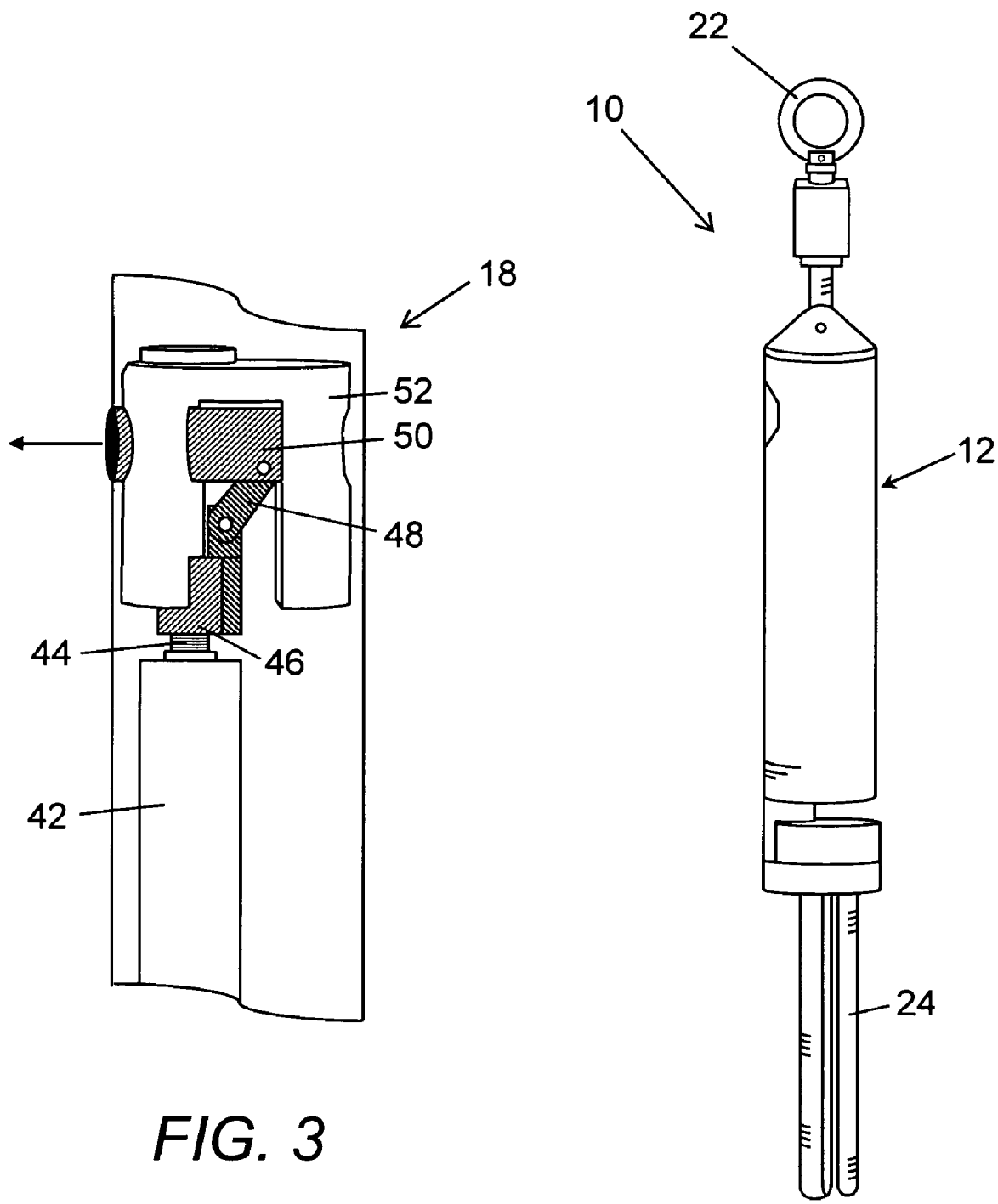
FIG. 3 depicts the adjustable-focus component 18 implemented in a camera robot of the present invention.
FIG. 4 shows a side view of a robot camera 10 in the collapsed view for insertion/retraction.

A variety of adjustable-focus components or mechanisms are known in the art and suitable for active or passive actuation of focusing in accord with the present invention. For example, one design employs the use of a motor and a lead screw. The motor turns a turn-table that is attached to a lead screw. A mating nut is attached to the imager. As the lead screw turns the imager translates toward and away from the lens that is mounted to the body of the robot. Alternatively, adjustable-focus component 18 is the actuation mechanism as depicted in FIG. 3, which employs a motor 42 that is directly connected to a lead screw 44 which is rotated by motor 42. As the lead screw 44 rotates it drives a lead nut 46 up and down. This up and down motion is translated by linkage 48 to a slider 50 that moves left to right. Slider 50 is held in place by a mechanism housing or guide 52. A lens or image sensor mounted to slider 50 can be translated back and forth from left to right to allow adjustable focusing.

The image sensor can be controlled from within the open space being viewed or externally to adjust image quality (e.g., color hues, white balance, saturation, etc.) to provide suitable feedback in conditions of low lighting. In particular embodiments, remote control of camera focus, as well as pan and tilt control is achieved using one or more controllers. Such controllers can be purchased from a commercial source (e.g., a directional pad, joystick or thumb stick), constructed de novo, or commercially available controllers customized to control the robotic components of the present invention. One skilled in the art is able to select a controller appropriate for the camera robot according to the present invention.

Video signal from the camera can be transmitted in any format (e.g., NTSC, digital, PAL, etc.) so long as it can be received and broadcast on a video monitor for viewing by the surgical team. For example, developments in solid state imaging of CMOS image sensors has enabled analog to digital conversion on each of the pixels within the pixel array. This type of improved CMOS imager includes transistors at every pixel to provide digital instead of analog output that enable the delivery of decoders and sense amplifiers much like standard memory chips. Further, the use of an over-sample converter at each pixel with a one bit comparator placed at the edge of the pixel array can be used instead of performing all of the analog to digital functions on the pixel. This design technology has been called MOSAD (multiplexed over sample analog to digital) conversion (Larish (September 1998) *Advanced Imaging*). The result of this process is low power usage, along with the capability to achieve enhanced dynamic range, possibly up to 20 bits. Another example of solid state imaging is disclosed in U.S. Pat. No. 6,020,581. This patent teaches an image sensor incorporating a plurality of detector cells arranged in an array wherein each detector cell has a MOSFET with a floating body and operable as a lateral bipolar transistor to amplify charge collected by the floating body. Alternatively, desktop personal and laptop computers can readily accomplish the necessary signal processing required to achieve a signal that can be displayed on a standard video monitor. The use of a computing device such as a desktop personal computer or a laptop computer enables relatively low cost cameras to be utilized as the imaging device. Those of ordinary skill in the art recognize that a signal from a camera can be processed to produce a display signal for many different types of display devices, including televisions configured to display an NTSC signal, televisions configured to display a PAL signal, cathode ray tube based computer monitors, LCD monitors, and plasma displays.

Depending on the internal environment in which the camera robot is used, the camera lens can be fitted with a component for cleaning the lens, e.g., a wiper blade or sacrificial film which is composed of multiple removable layers for maintaining a clear view of the internal environment.

To assure adequate lighting in the field of view, particular embodiments embrace a camera robot with a light source for illumination. The light source of the camera robot is proximate to the camera to provide constant or variable illumination for the camera. In particular embodiments, the light source is a component of a handle used for positioning the camera robot within the open space. As such, the light source illuminates the field of view as well as the handle. Any suitable commercially available light source can be employed. An exemplary light source is two 5 mm LEDs operating at 3.6 to 4 volts DC at 20 milliamps, provide 10,000 milli-candles of luminosity at a viewing angle of 20 degrees with 120 mW power dissipation. This amount of light is sufficient for in vivo viewing inside the abdominal cavity.

Advantageously, the camera robot is movably positionable within the surgical area so that when the position of the surgical tool(s) is changed, the position of the camera robot can be changed to continue to provide a video feed imaging the surgery. Movement of the camera robot enables a field of view obtained by the camera to be varied. Such movement enables the camera to obtain an image of at least a portion of the surgical area from a plurality of different angles without constraint by the entry incision. Accordingly, certain embodiments provide for a camera robot with a handle. In some embodiments the handle is rigid. In other embodiments, the handle is retractable. As depicted in FIG. 4, illustrative camera robot 10 is designed to collapse to fit inside a trocar during insertion into the open space of an animal and retraction from the animal's body. In the collapsed position, handle 22 is coaxial with robot body 12 of camera robot 10. Upon introduction into an open space, handle 22 can be deployed manually, mechanically actuated, or as exemplified herein spring loaded to rotate down 90 degrees as shown in FIGS. 1 and 2. Such passive actuation is achieved with torsion springs mounted to the handle at the axis of rotation. When in the deployed position, handle 22 is in the field of view of the camera 14 and illuminated by light source 16 so that the operator can readily see handle 22 in vivo and manipulate the position of the camera robot 10 or remove the camera robot 10 without the need of a second vision system (e.g., a laparoscope). In particular embodiments, the handle is in the shape of a ring or loop to facilitate manipulation.

For stability and weight distribution in vivo, the instant robot also has one or more support components. In some embodiments, the support component is retractable to minimize the size of the camera robot during insertion and retraction. Exemplary support components include, but are not limited to, legs, feet, skis or wheels to facilitate positioning and weight distribution of the instant camera robot within an open space (e.g., an abdominal cavity). As depicted in the illustrative camera robot of FIG. 4, support components 24 are legs, which in the collapsed position are coaxial with robot body 12 of camera robot 10. As with the handle, the support component can be deployed manually, or by mechanical actuation, or as exemplified herein spring loaded (e.g., with torsion springs) to rotate up 90 degrees as shown in the FIGS. 1 and 2. Moreover, the support component could be equipped with magnets such that the robot could be suspended upside down within the open space by placing a magnet external of the open space.

Certain embodiments embrace a wired or wireless camera robot, with wireless capabilities particularly desirable. Accordingly, power to the robot can be provided by an external tether, internal batteries, or a power unit placed within the open space being viewed. When wired or tethered, video images and commands can be transmitted via the tether. When the robot is wireless, an internal power supply is used, and the robot further contains a receiver and a transmitter. Versions of the camera robot of the present invention can use alkaline, lithium, nickel-cadmium, or any other type of battery known in the art. Alternatively, magnetic induction is another possible source of power, as is piezoelectrics. In addition, one of skill in the art could adapt other power sources such as fluid dynamic, solar or the like to power the robots of the present invention. Moreover, when employing a power unit placed inside the open space being viewed, the power unit can be used to supply power not only to one or more camera robots, but can also supply power to a family of surgical robots.

Receivers and transmitters useful in the present invention are many, such as those used on remote locks, such as for cars and other vehicles, other remote controls, and receiver and transmitter elements used in cell phones. Essentially, the input to the robot would be user command signals to the device, for example, to focus the camera, pan or tilt the body, or modulate lighting or sensor components. The output from the robot would be primarily data from the video or sensors.

In other embodiments of the present invention, the instant robot camera further contains sensors to measure, for example, temperature, pressure, presence of various gases and/or humidity or other parameters. Current minimally invasive surgical techniques, due to their remote nature, decrease the surgeon's ability to sense the surgical environment. A sensor-equipped camera robot according to this embodiment restores the surgeon's ability to perform more complex procedures, more accurately monitor patient health, and provide tissue diagnosis.

In particular embodiments, the camera robot is used in conjunction with standard laparoscopic surgical tools to create a system, whereby the camera robot is adapted to fit through a port of the laparoscopic surgical tool and used for obtaining an internal image of an animal, particularly the abdominal cavity of a human body. In general, an incision is made to access an open space inside the body of the animal (e.g., the abdomen), the camera robot of the instant invention is introduced into the open space of the animal's body and the internal space is illuminated and imaged to provide visual feedback to the surgical team.

In addition to use with surgical procedures conducted by medical doctors, it is also contemplated that the invention described herein has great utility with respect to oral surgery and general dental procedures wherein a very small imaging device can be used to provide an image of particularly difficult to access locations. Additionally, while the foregoing invention has application with respect to the medical and dental fields, it will also be appreciated by those skilled in the art that the camera robot set forth herein can be applied to other functional disciplines wherein the camera robot can be used to view difficult to access locations for industrial equipment and the like. Therefore, the camera robot of this invention could be used to replace many industrial boroscopes.

As indicated, the camera robot of the present invention can take on any configuration and be equipped with any number of sensors or attachments (e.g., arms or mirrors for obtaining additional views). There are hundreds of different components known in the art of robotics that can be used in the construction of the robot of the present invention; for example, there are hundreds of controllers, motors, power supplies, bodies, receivers, transmitters, cameras, and sensing devices that can be used in various combinations to construct a robot according to the present invention. In so far as the instant camera robot is useful for imaging inside the open space of a animal body cavity (e.g., the abdominal or thoracic cavity), the camera robot is made of any suitable biocompatible material which is easy to sterilize and sturdy enough so that the robot will not break inside the patient. Accordingly, particular embodiments provide that the camera robot components are produced from materials selected for being sterilizable. Suitable materials are well-known in the art of medical devices and include, but are not limited to, sterilizable plastics and/or metals.

The invention is described in greater detail by the following non-limiting examples.

EXAMPLE 1

Imaging Inside the Abdominal Cavity

Miniature camera robots were inserted through a small incision into an anesthetized pig and the abdominal cavity was then insufflated with carbon dioxide. The robotic cameras were used in conjunction with a standard endoscope and were moved to various locations within the abdominal cavity using standard laparoscopic tools. The wireless cylinder camera transmitted a video image to a monitor, while the pan and tilt robot camera's video feed was transmitted by wire to an additional screen. The surgeon then used these additional video cues to navigate the abdominal environment safely and effectively.

After the robots were inserted, the surgical team used the robots to plan and view trocar insertion and other laparoscopic port placement. The additional views from the in vivo cameras allowed the surgeon to plan and place trocars safely and appropriately in the abdominal cavity of the animal. The simple video images from these prototypes demonstrated how the surgeon could use such devices to view multiple areas of the surgical environment from several different angles.

The additional views provided additional frames of reference and perspectives that were not available with the endoscope alone. This allows for several points of view within the abdominal cavity, which proved useful to the surgeon while removing the pig's gallbladder. During the cholecystectomy, the robots were positioned to visually assist during the procedure. The miniature robots provided additional camera angles that augmented surgical visualization and improved orientation. This allowed the surgeon to have a better understanding of depth, improving safety and allowing the surgeon to plan and execute the procedure more effectively.

After using the in vivo robots to view the abdominal environment and trocar insertion, and to help plan and begin the gallbladder removal, the robots were removed from the abdomen by opening the pig along the mid-sagittal plane of the abdomen. The robots were then used, in addition to the endoscope, during the remainder of the cholecystectomy to visually assist the surgeon by providing additional visual cues, and alternate viewing angles.

What is claimed is:

1. A camera robot for surgical procedures, the robot comprising:
    (a) a body comprising a camera disposed within the body;
    (b) a rotation component pivotally coupled with the body, the rotation component comprising at least one of a pan component and a tilt component;
    (c) a handle coupled with a first end of the body; and
    (d) a non-attachable support component coupled with the body, wherein the body, rotation component, and support component are sized to fit within an animal body cavity.

2. The camera robot of claim 1, wherein the non-attachable support component comprises at least two legs.

3. The camera robot of claim 1, wherein the non-attachable support component comprises a foot.

4. The camera robot of claim 1, wherein the non-attachable support component is moveable between a collapsed position and a deployed position.

5. The camera robot of claim 1, wherein the non-attachable support component is a collapsible tripod.

6. The camera robot of claim 1, wherein the body further comprises an adjustable-focus component associated with the camera.

7. The camera robot of claim 1, wherein the body is substantially cylindrical.

8. The camera robot of claim 1, wherein the rotation component comprises the pan component and the tilt component.

9. The camera robot of claim 1, further comprising an external controller operably coupled with the robot.

10. The camera robot of claim 9, wherein the external controller is wirelessly coupled with the robot.

11. The camera robot of claim 1, further comprising a light source operably coupled with the body.

12. The camera robot of claim 11, wherein the light source is disposed on the handle.

13. The camera robot of claim 1, further comprising at least one sensor associated with the body.

14. The camera robot of claim 1, further comprising a power source operably coupled with the body.

15. A robotic camera system for surgical procedures, the system comprising:
    (a) a camera robot sized to fit within a body cavity of an animal, the robot comprising:
        (i) a body comprising a camera disposed within the body;
        (ii) a rotation component pivotally coupled with the body, wherein the rotation component comprises at least one of a pan component and a tilt component; and
        (iii) a handle coupled with a first end of the body;
        (iv) a non-attachable support component coupled with the body; and
    (b) an external controller coupled with the robot.

16. The system of claim 15, wherein the external controller is wirelessly coupled with the robot.

17. The system of claim 15, wherein the body further comprises an adjustable-focus component associated with the camera.

18. The system of claim 15, further comprising a power source operably coupled with the body.

19. The system of claim 15, wherein the non-attachable support component comprises at least two legs.

20. A camera robot comprising:
   (a) a body comprising a camera disposed within the body, the camera comprising:
      (ii) an image sensor operably coupled within the lens; and
      (iii) an adjustable-focus component coupled with the lens and image sensor;
   (b) a pan and tilt component comprising:
      (i) a connection component;
      (ii) a pivotal connection coupled with the body and the connection component; and
      (iii) a rotatable connection coupled with the connection component; and
   (c) a handle coupled with an end of the body; and
   (d) a support component coupled with the rotatable connection, wherein the support component is configured such that the component does not fixedly attach to any surface, and wherein the robot is sized to fit within an animal body cavity.

* * * * *